United States Patent [19]

Valenti

[11] Patent Number: 4,766,012

[45] Date of Patent: Aug. 23, 1988

[54] MICROENCAPSULATION OF A MEDICAMENT

[75] Inventor: Mauro Valenti, Magenta, Italy

[73] Assignee: Farmaceutici Formenti S.p.A., Milan, Italy

[21] Appl. No.: 899,147

[22] Filed: Aug. 22, 1986

[30] Foreign Application Priority Data

Aug. 29, 1985 [IT] Italy ................. 22009 A/85

[51] Int. Cl.$^4$ .................. A61K 9/58; A61K 9/62; B01J 13/02

[52] U.S. Cl. ................... 427/213.36; 424/461; 424/462; 424/494; 424/497; 428/402.24; 514/963

[58] Field of Search ............. 427/213.36; 428/402.24; 424/461, 462, 494, 497; 514/963

[56] References Cited

U.S. PATENT DOCUMENTS

| | | | |
|---|---|---|---|
| Re. 28,779 | 4/1976 | Katayama et al. | 264/4.3 X |
| 3,943,063 | 3/1976 | Morishita et al. | 428/402.24 X |
| 4,460,563 | 7/1984 | Calanchi | 428/402.24 X |

FOREIGN PATENT DOCUMENTS

| | | |
|---|---|---|
| 0130162 | 2/1985 | European Pat. Off. |
| 1483542 | 8/1977 | United Kingdom. |
| 1573361 | 8/1980 | United Kingdom. |

Primary Examiner—Richard D. Lovering
Attorney, Agent, or Firm—Cushman, Darby & Cushman

[57] ABSTRACT

The present invention relates to a process for the microencapsulation of a medicament by means of at least one coating agent, characterized in that is comprises the following steps:

(a) Dissolution of the coating agent in water, by salification;
(b) Dispersion of the particles of medicament to be microencapsulated, first in water, and then into the solution of the salified coating agent according to (a);
(c) Addition to the so-obtained suspension of an acidifying substance, which causes the precipitation of the coating agent onto the particles of medicament while these are being kept in suspension by stirring, thus microcapsules being formed.
(d) Recovery of microcapsules.

19 Claims, 2 Drawing Sheets

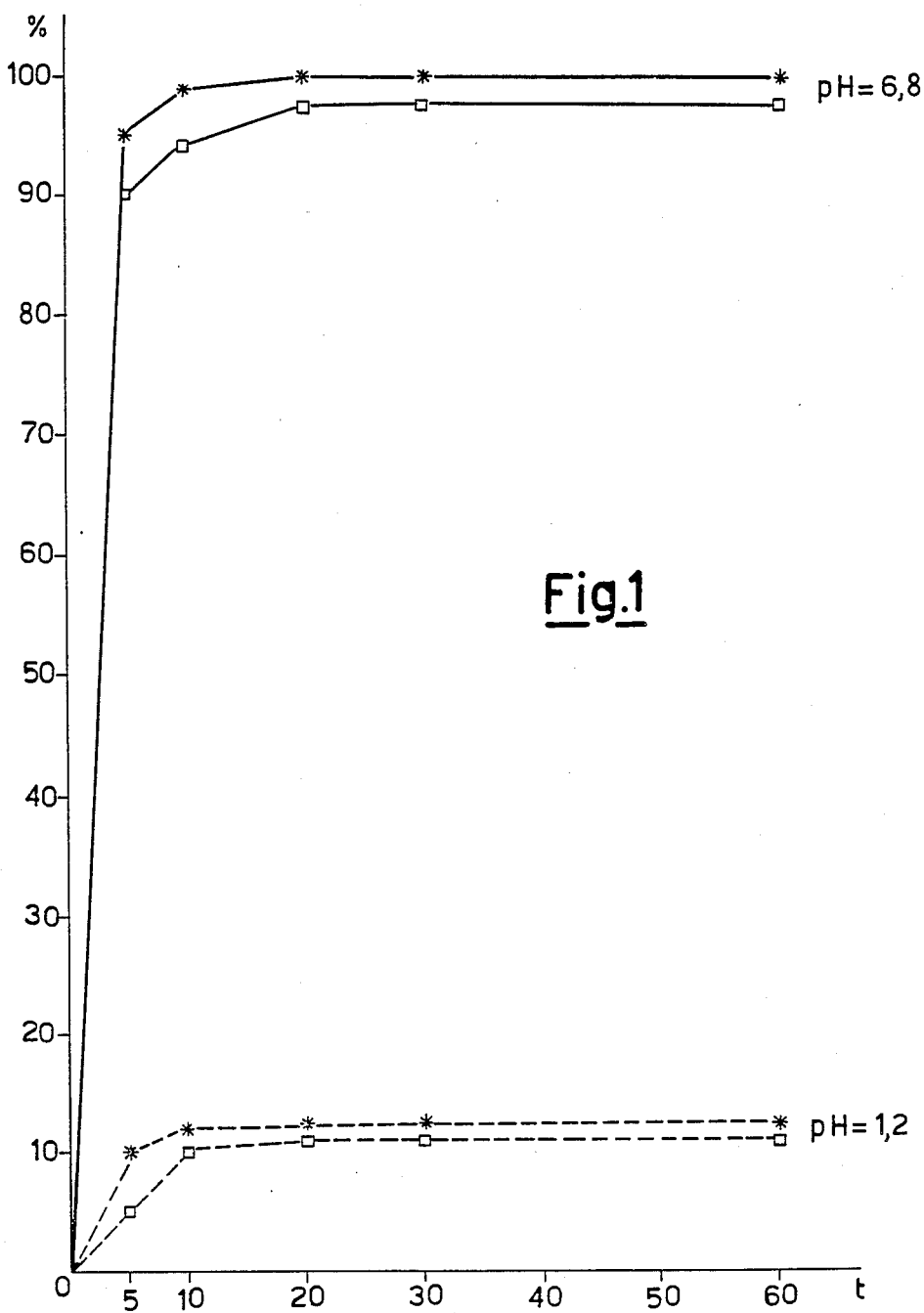

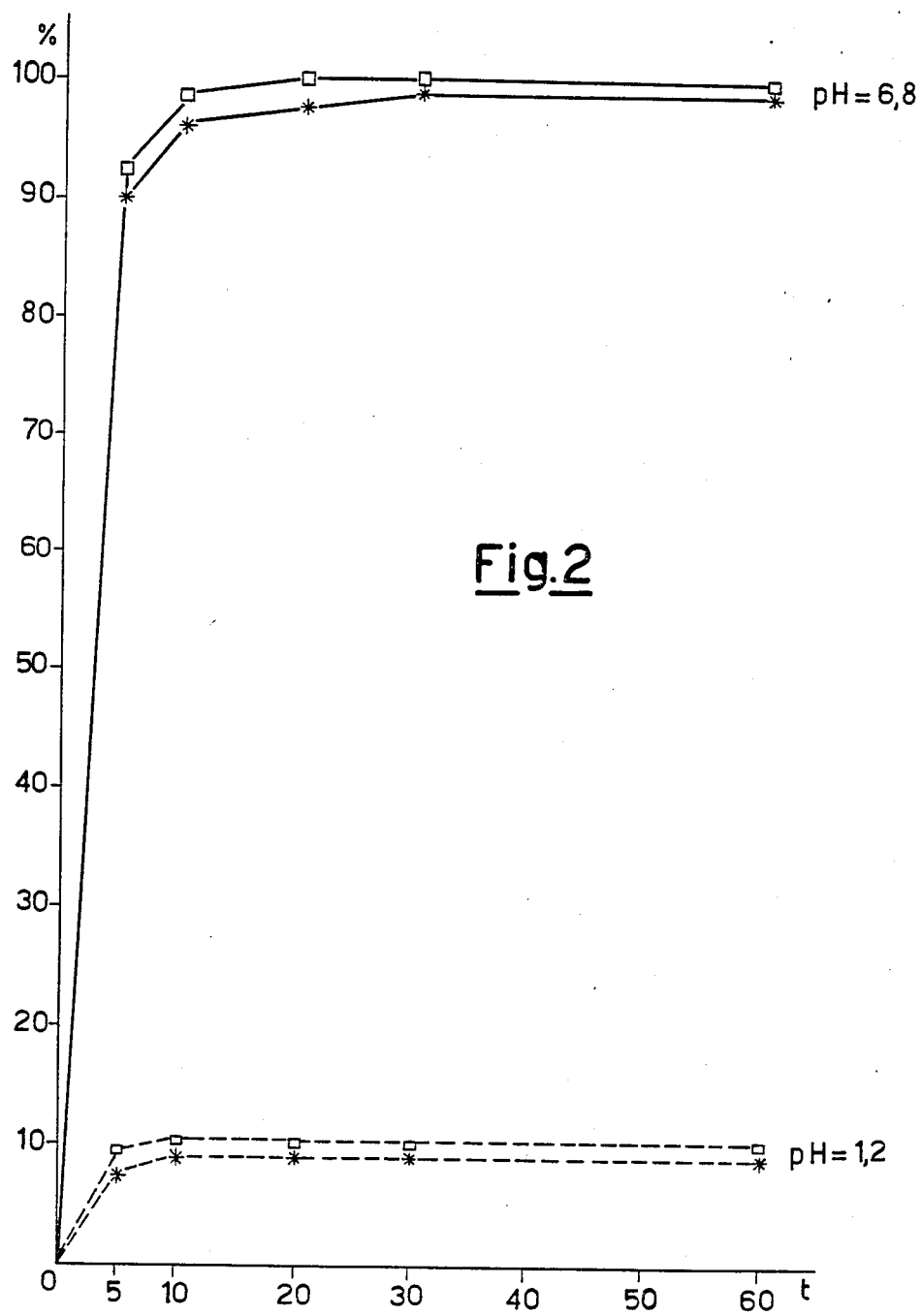

MICROENCAPSULATION OF A MEDICAMENT

The present invention relates to pharmaceutical preparations and more specifically to powders, granulates, and in general solid pharmaceutical forms containing a medicament in form of microcapsules, to the process for the production of microencapsulated medicaments, to the pharmaceutical formulations prepared by starting from the above said medicaments, and to the methods for the preparation of the same.

In the present discussion, by the term "medicament" an organic substance is meant, having a therapeutical usefulness and activity, whilst the term "microencapsulated medicament" relates to a particle, or to aggregates of particles of medicament, having more or less thin thickness, coated with a proper film-forming agent, of polymeric character, and having such mechanical characteristics as to withstand the normal manipulations adopted in the manufacturing of pharmaceutical forms.

Furthermore, when in the present discussion the term "classic pharmaceutical excipients" is used, reference is made to all those excipients normally used in the formulative field, to the purpose of improving the quality, or of facilitating the preparation of pharmaceutical forms, such as, for example: binders, lubricants, aromatizers, dyes, disintegrator agents, and so forth.

When the term "coating agent" is used, one or more polymers, gums or non toxic synthetic or natural rubbers are thereby meant, such as those normally used in formulative practice in pharmaceutical field.

Microencapsulation is a relatively recent technology, which allows particles of solids, or droplets of liquids to be coated, as single units or as aggregates, by substances of polymeric character, so to obtain microcapsules having sizes of the order of from 0.5 to 1000 microns.

This technology has been, and is still being the subject of a number of investigations in pharmaceutical field, in that it allows new systems to be obtained, able to release a medicament, to mask its bitter taste, and because it allows a better manipulation of the active principles highly sensible to atmospheric agents, or particularly aggressive towards the operators.

The most widely used microencapsulations techniques can be grouped in three classes:
(1) Methods using phase separation;
(2) Methods based on interfacial polymerization;
(3) Physical methods, such as centrifuging, extrusion, etc.

It must be observed however that the most of the microencapsulation methods use the phase separation technique.

The concept on which they are based, consists essentially in submitting to coacervating a solution of a colloid (for example, gelatin or gum arabic), wherein the powder to be microencapsulated has been suspended by one of the possible available techniques such as, for example, temperature changes, pH variations, solubility changes, etc.

The coacervation which is thus formed tends to coat the medicament particles kept suspended in a suitable carrier, wherein they are insoluble, thus forming microcapsules.

This technique, precisely denominated "coacervating technique" is rather laborious and shows a certain number of difficulties; for example, a critical step is represented by the recovery of the microcapsules and their drying.

In fact, in most cases, instead of microcapsules, obtained is a shapeless coacervation, difficult to be filtered off and which must be subsequently dried by particular techniques, such as atomization, freeze-drying, fluidized bed, or by washing with dehydrating solvents.

In case the technique of coacervating in organic solvents is used, besides the inflammability risk, also the problem occurs of the complete removal of the solvent, which must be carried out in vacuo, and at controlled temperature. Finally, according to the type of colloids used, gastro-soluble microcapsules, or gastroresistant, entero-soluble microcapsules can be obtained.

Purpose of the present invention is mainly solving the above discussed problems, with reference to the known technique of phase separation.

Among others, the present invention intends, in particular, providing microcapsules of regular shape, having small diameter and completely free from smell and taste.

For the accomplishment of these purposes, the present invention proposes a process for the microencapsulation of a medicament by means of at least one coating agent, characterized in that it comprises the following steps:

(a) Dissolution of the coating agent into water, by salification;
(b) Dispersion of the particles of medicament to be microencapsulated first in water, and then in the solution of the salified coating agent according to (a);
(c) Addition to the so-obtained suspension of an acidifying substance, which causes the precipitation of the coating agent onto the particles of medicament while these are being kept in suspension by stirring, thus microcapsules being formed.
(d) Recovery of the microcapsules.

The process of the invention is now described in greater detail.

First of all, the coating agent/s using which is desired (e.g., hydroxypropylmethylcellulose) is/are dissolved in a volume of purified water equal to 1/5–1/10 of the total volume, and in which sodium hydroxide, or any other basis, has been previously dissolved, in stoichiometric amount relatively to the amount of coating agent.

Separately, in the residual volume of purified water, the medicament to be microencapsulated is suspended.

If needed, homogenizing the suspension by a turbine or a high-velocity turboemulsifier (e.g., 3000 r.p.m.) is useful to better disperse possible clots of medicament.

The suspension of medicament is then added to the solution of coating agent, while this is being kept stirred, and stirring is continued until a homogeneous suspension is obtained.

As stirrer, the use is recommended of a normal blade-stirrer, the revolution velocity of which be adjustable within the range of from 100 to 1000 r.p.m., preferably within the range of from 300 to 800 r.p.m.

After the end of the addition, stirring the resulting suspension is continued at a velocity of from 400 to 600 r.p.m., so that pH of suspension may stabilize within the range of from 5.6 to 6.0, preferably of from 5.7 to 5.9.

Under these conditions, the coating agent is still completely in solution, whilst the the most of the medicament is in suspension.

It may happen in some cases that a minimum amount of medicament goes into solution, but the subsequent lowering in pH makes precipitate also the portion of the medicament possibly gone dissolved.

At this point, the microencapsulation is carried out of the particles kept suspended by adding dropwise a solution of hydrochloric acid having a concentration comprised within the range of from 0.1N to 1N, preferably within the range of from 1N to 5N. The acid addition rate must be so adjusted that pH of suspension decreases at a rate comprised within the range of from 0.001 to 1 units per second, preferably of from 0.005 to 0.1 unit per second.

Under these conditions, the suspended particle act as half-nuclei, around which the polymer particles deposit.

The precipitation of coating agent takes place very slowly up to pH 3.5–4.0, then a sharp pH jump occurs, which corresponds to the macroprecipitation of polymer onto particles.

At this point, stirring is continued for some minutes, stirring is then discontinued and suspension is allowed to decant.

The obtained product is finally filtered off and dried.

The dimensions of microcapsules which are obtained depend on the stirring rate at which the suspension is maintained: the slower the stirring, the greater the dimensions of microcapsules, and vice-versa.

The coating agent can be selected among all those polymers of organic character which are completely soluble in water at pH higher than 5.0 and which are insoluble at pH values lower than 5.0.

The coating agents having such characteristics can be:

(A) Polymers of carboxyalkyl-alkylcellulose type; or hemi-esters of organic dicarboxy acids (e.g., the phthalic of succinic hemi-esters of an alkylcellulose, of a hydroxy-alkyl-alkylcellulose or of cellulose acetate)
Examples: methylcellulose phthalate; hydroxypropylmethylcellulose phthalate; hydroxypropylmethylcellulose succinate; hydroxyethyl-ethylcellulose phthalate; cellulose aceto phthalate; cellulose aceto succinate.

(B) Copolymers of an alkenyl carboxy acid and of an alkyl ester of an alkenyl carboxy acid
Examples: Methacrylic acid—methyl methacrylate copolymer; methacrylic acid—methyl acrylate copolymer; methacrylic acid—ethyl acrylate copolymer.

(C) Copolymers of an alkenyl carboxy acid and of two alkyl esters of an alkenyl carboxy acid
Examples: Methacrylic acid—methyl acrylate—methyl methacrylate copolymer; methacrylic acid—methyl methacrylate—ethyl methacrylate copolymer; methacrylic acid—methyl methacrylate—octyl acrylate copolymer.

For the preparation of the microcapsules according to the present invention, the amount of coating agent to be used must be comprised within the range of from 0.01 to 5.0 g, preferably of about 0.05–2.5 g per gram of medicament.

Among the different salifying agents which can be used, all the most common organic and inorganic bases and the inorganic salts of basic character commonly used in chemical field can be listed, such as, for instance:

(A) Bases of alkali and alkali-earth metals: sodium hydroxide, potassium hydroxide, magnesium hydroxide, calcium hydroxide; etc.;
(B) Ammonia, as ammonium hydroxide;
(C) Alkylamines: triethylamine, diethylamine, trimethylamine, methylamine, dimethylamine, isopropylamine, etc.;
(D) Alkyletheramines: triethanolamine, diethanolamine, etc.;
(E) Inorganic salts of basic character: disodium monohydrogen phosphate, dipotassium monohydrogen phosphate, etc.

The present invention can be applied to a wide range of medicaments. A medicament, in order to be suitable to be microencapsulated according to the present invention, must have the following chemical-physical characteristics:

it must be a solid having a granulometry comprised within the range of from 5 to 1000 microns, preferably of from 5 to 500 microns;
it must be insoluble or very poorly soluble in aqueous solutions at pH values lower than 5.0.

Examples of medicaments which can be used can be selected from the following thepapeutical classes:

Non-steroidic antiinflammatory-analgaesic drugs: Paracetamol, flufenamic acid and mefenamic acid, Ibuprofen, Flurbiprofen, Naproxene, Ketoprofen, Phenylbutazone, Indomethacin and derivatives;
Hypotensive drugs: Captopril, Methyldopa;
Antibiotics: Amoxicillin, Ampicillin, Cephalexin, Chloramphenicol, Erithromycin and derivatives, Fosfomycin;
Sulphamidics: Sulfamerazine, succinyl-sulfathiazole, sulfadimethoxine, sulfamethoxazole, sulfathiazole, trimethroprim.

The precipitation of the coating agent on the suspended particles of medicament can be accomplished by acidification by one of the following inorganic acids:
Hydrochloric acid;
Phosphoric acid;
Sulphuric acid.

To the purpose of better understanding characteristics and advantages of the invention, hereunder non-limitative examples of practical embodiments thereof are illustrated.

As to Example 1, reference is made to the figures of the accompanying drawings, which show release curves according to the explanations given hereinafter.

EXAMPLE 1

Medicament to be microencapsulated: IBUPROFEN having the following characteristics:
apparent density: 0.3 g/ml
granulometric distribution:
1.9% greater than 125 microns
3.4% comprised within 125–90 microns
7.1% comprised between 90–75 microns
87.6% smaller than 75 microns
Coating agent: HYDROXYPROPYLMETHYLCELLULOSE PHTHALATE having the following characteristics:
methoxy content: 20%
hydroxypropyl content: 7%
carboxymethyl content: 31%
complete solubility at pH values higher than 5.5

Operating Method

Into a vessel of about 10 l of capacity introduced is:

| | | |
|---|---|---|
| purified water | ml | 600.000 |
| and into it: | | |
| potassium hydroxide | g | 7.500 |
| is dissolved with stirring. | | |
| At complete solution: | | |
| hydroxypropylmethylcellulose phthalate | g | 50.000 |

-continued is introduced.

Into a separate vessel of about 10 l of capacity introduced is:

| purified water | ml | 5000.000 |
|---|---|---|
| then | | |
| Ibuprofen | g | 950.000 |
| is dispersed with stirring (500 r.p.m.). | | |

The resulting suspension is then homogenized by the ULTRA TURRAS turboemulsifier adjusted at a velocity of about 3000 r.p.m.

To the solution prepared in (1), the suspension prepared in (2) is slowly added, and the whole is kept stirred at 600 r.p.m. at 20° C. for about 20 minutes. Subsequently, with the stirring velocity being kept at 600 r.p.m., 135 ml of 1N solution of hydrochloric acid is added.

Stirring is continued for a further 15 minutes, the suspension is decanted, the clear supernatant is removed, the suspended matter is then filtered off and is dried in air-circulation oven for 8 hours at 40° C.

After drying, microencapsulated Ibuprofen is passed through a sieve with 0.5 mm mesh (free opening) and is finally connected inside polythene bags. By the above-reported technique, different batches of microencapsulated Ibuprofen have been prepared, with increasing amounts of hydroxypropylmethylcellulose phthalate (10%-20%).

The microencapsulated products obtained have been analyzed for chemical composition, by using the analytical methods as reported in U.S. Pharmacopoeia XXIst, page 526, relating to Ibuprofen. The results obtained are reported in Table 1.

TABLE 1

| | PREPARATION No. 1 | PREPARATION No. 2 | PREPARATION No. 3 |
|---|---|---|---|
| Amount of Coating Agent | 5% | 10% | 20% |
| Theoretical Batch | 1000 g | 1000 g | 1000 g |
| Practical Yield | 95% | 96% | 97.5% |
| Ibuprofen Content/100 g | 94.5 g | 90.5 g | 81.15 g |
| Moisture | 0.5% | 0.4% | 0.5% |
| Apparent density | 0.41 g/ml | 0.43 g/ml | 0.45 g/ml |
| Granulometric Distribution | | | |
| >125μ | 0.5% | 0.2% | 0.2% |
| <125μ  >90μ | 1.0% | 2.1% | 2.5% |
| <90μ  >75μ | 7.0% | 6.3% | 4.9% |
| <75μ | 91.5% | 91.4% | 92.4% |
| Organoleptic Characters | Odourless, tasteless white powder | Odourless, tasteless white powder | Odourless, tasteless white powder |

By using both microencapsulated Ibuprofen, obtained as described above, and untreated Ibuprofen, solid pharmaceutical forms for oral administering have been prepared, as extemporaneous granular products, and of tablets containing 600 mg/dose of Ibuprofen.

For all the formulations, the bioavailability in vitro and in vivo has been evaluated.

For the performing of the in-vitro test, used has been the equipment No. 2 as disclosed in U.S.P. XXIst, page 1243, adjusted at 150 r.p.m., and as the dissolving means, buffer solutions at pH 1.2 and 6.8 have been used.

The draws have been carried out at 5—10—20—30—60 minutes, and the dissolved amount of Ibuprofen has been determined by H.P.L.C. method, by using a C8 10-μ 25-cm long reverse-phase column having an inner diameter of 4.6 mm and a mobile phase constituted by (40:60) acetonitrile/water buffered at pH 3.0 with phosphoric acid, detection wavelength 220 nm.

BRIEF DESCRIPTION OF THE DRAWINGS

The charts obtained are reported at FIGS. 1 and 2.

FIG. 1 shows the release curve of the extemporaneous granular composition containing Ibuprofen microencapsulated with 10% of HPMC-P (□), as compared to an extemporaneous granular composition containing non-microencapsulated Ibuprofen (*).

FIG. 2 shows the release curve of the tablets containing 600 mg of Ibuprofen microencapsulated with 5% of HPMC-P (□), as compared to tablets containing non-microencapsulated Ibuprofen (*).

In such charts, on the ordinates the released percentage of Ibuprofen, and on the abscissae the time in minutes is reported.

The in-vivo bioavailability of the pharmaceutical forms has been evaluated on rabbit.

The haematic levels obtained for both the pharmaceutical forms containing microencapsulated Ibuprofen, and those containing untreated Ibuprofen, have resulted perfectly overlapping to each other and in good agreement with the values observed by the in-vitro tests.

Acceptability tests have also been carried out by the double-blind method, by comparing a preparation of extemporaneous granular compositions, containing 600 mg of microencapsulated Ibuprofen in an aromatized sugar carrier, to a similar preparation containing untreated Ibuprofen.

The formulation containing microencapsulated Ibuprofen has been the one by far preferred by the subject taking part to the test.

As for the tablet-form formulation, it should be underlined that by using microencapsulated Ibuprofen, accomplishing was possible, by direct pressing, tablets having an Ibuprofen:excipients ratio of 83.17, and complying with the specifications as provided by European Pharmacopoeia.

In the tablets which can be manufactured with non-microencapsulated Ibuprofen, and which can be accomplished by humid way only, the minimum Ibuprofen:Excipients ratio, necessary to obtain tablets complying with the specifications of European Pharmacopoeia, is of 65:35.

This means that, with the content of Ibuprofen being the same, the tablets as prepared by starting from microencapsulated Ibuprofen weigh about 22% less than tablets as prepared from non-microencapsulated Ibuprofen, and allow a cheaper process to be accomplished, by being obtainable by the direct pressing of powders blend.

EXAMPLE 2

Medicament to be microencapsulated: IBUPROFEN having the same characteristics as described at Example 1.
Coating agent: CELLULOSE ACETO PHTHALATE having the following characteristics:
acetyl group ($C_2H_3O$): 22%
phthalyl carboxybenzoyl group: 33%

Method

Microcapsules have been prepared by following the same route as described at Example 1, but with the difference that 50.00 g of cellulose aceto-phthalate has been used in lieu of hydroxypropylmethyl cellulose phthalate.

The microencapsulated medicament obtained has been analyzed for chemical composition, by using the analytical methods as reported in U.S.P. XXIst, page 526, relating to Ibuprofen.

The results obtained are reported in Table 2.

TABLE 2

| | |
|---|---|
| Amount of coating agent | 5% |
| Theoretical Batch | 1000 g |
| Practical Yield | 97% |
| Ibuprofen content/100 g | 94.5 g |
| Moisture | 0.6% |
| Apparent Density | 0.335 g/ml |
| Granulometric Distribution | |
| >125μ | 3.36% |
| <125μ  >90μ | 4.85% |
| <90μ  >75μ | 7.42% |
| <75μ | 84.5% |
| Organoleptic Characters | Odourless, tasteless white powder |

As for the in-vitro bioavailability, it has been seen that the amount of Ibuprofen which is dissolved in artificial gastric juice after 60 minutes is lower than 10%, whilst in enteric juice (pH 6.8) the release is achieved of 100% within 12 minutes.

EXAMPLE 3

Medicament to be micro-encapsulated: FLURBIPROFEN having the following characteristics:
Apparent Density: 0.272 g/ml
Granulometric Distribution:
7.3% greater than 125 microns
30.57% comprised within 125–90 microns
39.54% comprised between 90–75 microns
22.50% smaller than 75 microns
Coating agent: HYDROXYPROPYLMETHYLCELLULOSE PHTHALATE having the same characteristics as described at Example 1.

Method

The microcapsules have been prepared by using the same method as described at Example 1, but with the difference that 950.000 g of Flurbiprofen has been used in lieu of Ibuprofen.

For Flurbiprofen too, different batches of microencapsulated product have been prepared with increasing amounts: 5–10 and 20%, of hydroxypropylmethylcellulose phthalate.

The titre in Flurbiprofen per gram of microencapsulated product has been determined by the same H.P.L.C. method as described at Example 1 for Ibuprofen determination.

The results obtained are shown in Table 3.

TABLE 3

| | PREPARATION No. 1 | PREPARATION No. 2 | PREPARATION No. 3 |
|---|---|---|---|
| Amount of Coating Agent | 5% | 10% | 20% |
| Theoretical Batch | 1000 g | 1000 g | 1000 g |
| Practical Yield | 96.5% | 94.8% | 95.5% |
| Flurbiprofen Content/100 g | 95.2 g | 89.4 g | 80.5 g |
| Moisture | 0.6% | 0.4% | 0.5% |
| Apparent density | 0.37 g/ml | 0.35 g/ml | 0.347 g/ml |
| Granulometric Distribution | | | |
| >125μ | 11.20% | 5.0% | 22.0% |
| <125μ  >90μ | 10.58% | 4.8% | 4.6% |
| <90μ  >75μ | 46.79% | 9.4% | 5.7% |
| <75μ | 31.35% | 80.7% | 67.7% |
| Organoleptic Characters | Odourless, tasteless white powder | Odourless, tasteless white powder | Odourless, tasteless white powder |

With the microencapsulated product, pharmaceutical forms have been prepared as extemporaneous granular product, the in-vitro bioavailability of which has been evaluated.

Both by using microencapsulated Flurbiprofen with titre 80.5% and the one with 95.2% titre, the amount of active principle released in artificial gastric juice within a 60 minutes time is lower than 15%, whilst in enteric juice (pH 6.8), the release is achieved of 100% within about 10 minutes.

EXAMPLE 4

Medicament to be microencapsulated: IBUPROFEN having the same characteristics as described at Example 1.
Coating agent: ANIONIC COPOLYMER composed by METHACRYLIC ACID—METHYL METHACRYLATE—ETHYL METHACRYLATE having a 1:1 ratio of free to esterified carboxy groups.
Molecular Weight: 250,000

Method

The microcapsules have been prepared by using the same route as described at Example 1, but with the difference that 10.00 g of anionic copolymer of methacrylic acid—methyl methacrylate—ethyl methacrylate instead of hydroxypropylmethylcellulose phthalate and 200 g of Ibuprofen has been used.

The microencapsulated product has been analyzed according as described in U.S.P. XXIst, page 526, relating to Ibuprofen.

The results obtained are reported in Table 4.

TABLE 4

| | |
|---|---|
| Amount of coating agent | 10% |
| Theoretical Batch | 200 g |
| Practical Yield | 95.2% |
| Ibuprofen content/100 g | 95.8 g |
| Moisture | 0.3% |
| Apparent Density | 0.333 g/ml |
| Granulometric Distribution | |
| >125μ | 3.57% |
| <125μ  >90μ | 5.0% |
| <90μ  >75μ | 7.1% |
| <75μ | 84.33% |
| Organoleptic Characters | Odourless, tasteless white powder |

The in-vitro bioavailability tests have been performed according to the method as described at Example 1.

As for the in-vitro bioavailability, it has been seen that the amount of Ibuprofen which is dissolved in artificial gastric juice after 60 minutes is lower than 10%, whilst in enteric juice (pH 6.8), the release is achieved of 100% after 5 minutes.

In general, the advantages deriving from the present invention are basically as follows:

The manufacturing process is extremely simple, easy and quick to be performed.

The equipment required by the manufacturing is of traditional type; only the availability of a dissolver equipped with stirrer with velocity adjustable between 100 and 1000 r.p.m. is needed.

Easy to be found out is also the filter necessary for the recovery of microcapsules, which can be selected among a wide range of equipment for filtration, normally used in pharmaceutical field.

The equipment for the end drying can be selected as desired among a static oven, a fluidized bed, or any other drying systems. All the equipments necessary for the accomplishment of the present microencapsulation process can be easily found and is available by any pharmaceutical laboratory.

The manufacturing method as disclosed, differently to the most of the other methods, does not require heating steps, thus allowing a higher cheapness in process.

The present microencapsulation method is carried out in the aqueous phase, with the complete exclusion of organic solvents.

This renders safe and cheap this method, prevents incurring the problems arising from the use of organic solvents, and eliminates the need for particular explosion-proof and pollution-preventing installation.

The present microencapsulation method allows the medicament processed to be recovered as microcapsules, with a yield higher than 90%.

This microencapsulation methodology allows medicament-containing tasteless, odourless microcapsules to be obtained, having sizes falling within the same granulometric range as of the starting raw material. In any case, by suitably optimizing the mixing velocity, and adopting a proper homogenizing, the present method allows microcapsules to be obtained in dimensions not exceeding by more than 10% the dimensions of the starting particles.

Furthermore, the microencapsulation of medicaments which have the form of very light powder, allows microcapsules to be obtained, which too have small dimensions, but with better rheologic characteristics: for example, apparent density, better free-flowing characteristics, narrower granulometric range, better dispersibility in the pharmaceutical excipients used for the formulation, mixture with homogeneous content of active principle, and so forth.

The improvement in rheologic characteristics of a medicament also allows manufacturing methods to be adopted, for the solid pharmaceutical forms which can be derived from such medicaments, much cheaper than the direct pressing in case of tabletted pharmaceutical forms, the direct mixing with the excipients in case of pharmaceutical preparations in form of extemporaneous granular products, the fractional subdivision of the medicament directly inside the packing container (e.g., granular forms for extemporaneous suspensions), the direct subdivision of microencapsulated medicament in case of pharmaceutical forms in rigid operculated capsules.

Furthermore, the increase in apparent density of the microencapsulated medicament allows solid pharmaceutical forms, e.g., tablets, to be formulated in smaller dimensions than the same pharmaceutical forms obtainable with non-microencapsulated active principles and hence, in case of high-dosage medicaments, improves the assumption thereof by the users.

The microcapsules produced by this microencapsulation method maintain their chemical-physical characteristics unchanged over time; nor does the medicament therein contained suffer any alterations, whether of chemical type, or of pharmaco-biological type.

The bioavailability of the medicaments undergoing this type of microencapsulation remains unchanged; moreover, some medicaments, such as, e.g., the non-steroidic antiinflammatory drugs of acidic character, such as Flurbiprofen, Ibuprofin, and so forth, and of which known are the gastroinjuring properties, when submitted to this type of microencapsulation, yield better tolerated pharmaceutical forms than the same pharmaceutical forms prepared from non-microencapsulated medicaments.

I claim:

1. A process for the microencapsulation of a medicament by at least one coating agent consisting essentially of the steps of:
   (a) dissolving the coating agent in water by salification, whereby a solution is formed;
   (b) dispersing particles of the medicament to be microencapsulated first in water and then in the solution of salified coating agent obtained in step (a), whereby a suspension is formed;
   (c) adding an acidifyig substance to the suspension obtained in step (b) so that the coating agent precipitates onto the particles of medicament kept in suspension by stirring, whereby microcapsules are formed; and
   (d) recovering the microcapsules.

2. The process as claimed in claim 1, wherein the coating agent is selected from the group consisting of a carboxyalkyl-alkylcellulose; a hemiester of an organic dicarboxy acid of an alkyl cellulose or of a hydroxyalkyl-alkyl cellulose or of cellulose acetate; a copolymer of an alkenylcarboxy acid and an alkyl ester of an alkenyl carboxy acid; a copolymer of an alkenyl carboxy acid and two alkyl esters of an alkenyl carboxy acid; a phthalic or succinic hemiester of an alkyl cellulose or of a hydroxyalkyl-alkyl cellulose or of cellulose acetate; a copolymer formed by an acrylic or methacrylic acid and an alkyl ester of an acrylic or methacrylic acid; a copolymer composed by an acrylic and methacrylic acid and by an alkyl acrylate or by an alkyl methacrylate; a copolymer of methacrylic acid and of an alkyl acrylate; a copolymer of methacrylic acid and alkyl methacrylate; a copolymer of methacrylic acid-alkyl acrylate-alkyl methacrylate; and a copolymer of methacrylic acid-alkyl methacrylate-alkyl methacrylate.

3. The process according to claim 2, wherein the alkyl group has one to four carbon atoms.

4. The process according to claim 2, wherein the alkenyl group has 3 or 4 carbon atoms.

5. The process according to claim 1, wherein the coating agent is selected from the group consisting of a carboxymethylethyl cellulose; cellulose aceto-phthalate; hydroxypropyl methylcellulose phthalate; and a copolymer of methacrylic acid.

6. The process according to claim 1, wherein in step (a),
the coating agent is dissolved in previously alkalified water.

7. The process according to claim 1, wherein the concentration of the coating agent in solution is within the range of from 0.05% to 43% weight/weight.

8. The process according to claim 7, wherein the concentration of the coating agent in solution is within the range of from 0.1% to 27% weight/weight.

9. The process according to claim 1, wherein the amount of coating agent/gram of medicament used is within the range of from 0.01 to 5 g.

10. The process according to claim 9, wherein the amount of coating agent/gram of medicament used is within the range of from 0.05 to 2.5 g.

11. The process according to claim 1, wherein the particles of medicament are within the range of from 5 to 1000 microns in size.

12. The process according to claim 11, wherein the particles of medicament are within the range of from 5 to 500 microns in size.

13. The process according to claim 1, wherein the medicament has the form of a solid.

14. The process according to claim 1, wherein the medicament is insoluble in water or in aqueous solutions at pH values lower, than 5.

15. The process according to claim 1, wherein the solubilization of the coating agent is obtained by salification with an inorganic base or with the salt of an inorganic base.

16. The process according to claim 15, wherein the solubilization of the coating agent is obtained by salification with an inorganic base.

17. The process according to claim 1, wherein the precipitation of the coating agent on the medicament particles is obtained by acidification with an inorganic acid.

18. The process according to claim 17, wherein the precipitation of the coating agent is obtained by acidification with a solution of hydrochloric acid having a concentration within the range of from 0.1N to 1N.

19. The process according to claim 17, wherein the precipitation of the coating agent is obtained by acidification with a solution of hydrochloric acid having a concentration within the range of from 1N to 5N.

* * * * *